United States Patent [19]

Reiter

[11] Patent Number: 4,814,341

[45] Date of Patent: Mar. 21, 1989

[54] 2-GUANIDINO-4-(2-FURYL) THIAZOLES AS ANTIULCER AGENTS

[76] Inventor: Lawrence A. Reiter, 32 West Mystic Ave., Mystic, Conn. 06355

[21] Appl. No.: 185,249

[22] Filed: Apr. 19, 1988

Related U.S. Application Data

[63] Continuation of Ser. No. 918,946, Aug. 26, 1986, abandoned.

[51] Int. Cl.$^4$ ................. C07D 417/04; A61K 31/425
[52] U.S. Cl. ..................................... 514/370; 548/193
[58] Field of Search ......................... 548/193; 514/370

[56] References Cited

U.S. PATENT DOCUMENTS

| | | | |
|---|---|---|---|
| 3,950,333 | 4/1976 | Durant et al. | 260/250 |
| 4,128,658 | 12/1978 | Price et al. | 464/285 |
| 4,315,009 | 2/1982 | Jones et al. | 424/248.4 |
| 4,374,843 | 2/1983 | LaMattina et al. | 424/270 |
| 4,435,396 | 3/1984 | LaMattina et al. | 424/248.51 |

FOREIGN PATENT DOCUMENTS

| | | |
|---|---|---|
| 59-225186 | 12/1984 | Japan . |
| 896495 | 5/1962 | United Kingdom . |
| 2060607 | 5/1981 | United Kingdom . |

Primary Examiner—Robert Gerstl

[57] ABSTRACT

A series of novel thiazole compounds, having a guanidino or substituted guanidino group at the 2-position and a 5-(N,N-disubstituted aminomethyl)-2-furyl group at the 4-position. The compounds of the invention are useful for administration to mammals for prophylactic or curative treatment of peptic ulcers.

13 Claims, No Drawings

2-GUANIDINO-4-(2-FURYL) THIAZOLES AS ANTIULCER AGENTS

This is a continuation of application Ser. No. 918,946 filed Aug. 26, 1986 now abandoned.

TECHNICAL FIELD

Gastric and duodenal ulcers, collectively known as peptic ulcers, are common afflictions of mammals, especially humans, and they cause much distress in form of pain and in severe cases internal bleeding. A variety of methods have been recommended for inhibiting (i.e., preventing or curing) peptic ulcers, such as careful control of diet, drug therapy, and in some cases surgical intervention.

Modern methods of drug therapy for inhibiting peptic ulcers have focussed on blocking the so-called histamine $H_2$-receptors. Histamine is a physiologically-active substance which occurs naturally in mammalian species, and it is believed to exert its biological effects by binding to certain sites known as histamine receptors. Two types of such receptors are known; namely, histamine $H_1$-receptors and histamine $H_2$-receptors. When histamine binds to an $H_1$-receptor in a mammalian subject, this leads to the appearance of allergic responses such as bronchospasm or allergic rhinitis; while when histamine binds to an $H_2$-receptor this leads to increased secretion of gastric acid. Since gastric hyperacidity causes or exacerbates peptic ulcers, attempts have been made to find chemical substances which block histamine $H_2$-receptors in an effort to develop new drugs having utility as antiulcer agents. Such chemical substances are often called histamine $H_2$-antagonists.

BACKGROUND ART

Two agents which have found use recently in clinical practice as histamine $H_2$-antagonists are cimetidine (U.S. Pat. No. 3,950,333) and ranitidine (U.S. Pat. No. 4,128,658), the compounds having the following chemical formulae:

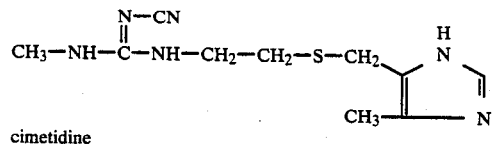

cimetidine

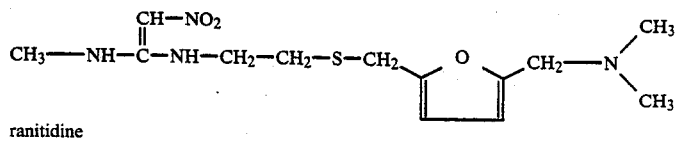

ranitidine

In addition, certain chemical substances are valuable as antiulcer agents in mammals by virtue of their so-called cytoprotective activity. These agents can be recognized by their ability to inhibit the formation of gastric ulcers in rats which have been dosed orally with large amounts of ethanol.

U.S. Pat. Nos. 4,374,843 and 4,435,396 disclose 2-guanidino-4-heteroarylthiazole compounds having antiulcer activity.

Disclosure of Invention

However, despite recent advances in the drug therapy of peptic ulcers, there is a need for new agents.

Accordingly it is the object of the present invention to provide a series of new chemical compounds which can be used in mammals as antiulcer agents. These new chemical compounds are 2,4-disubstituted thiazole compounds, in which the 2-substituent is a guanidino or substituted guanidino group, and the 4-substituent is a 5-(N,N-disubstituted aminomethyl)-2-furyl group.

More particularly, the invention provides new 2-guanidino-4-(2-furyl)thiazole compounds of the formula

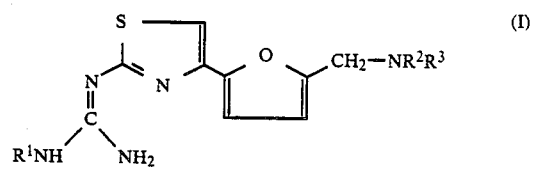

and the pharmaceutically-acceptable acid-addition salts thereof, wherein $R^1$ is selected from the group consisting of hydrogen, alkyl having 1 to 6 carbons and $-(CH_2)_m-W$;

$R^2$ is alkyl having 1 to 6 carbons; and $R^3$ is alkyl having 1 to 6 carbons or $-(CH_2)_n-Z$;

wherein m and n are each 1, 2 or 3; and W and Z are each selected from the group consisting of phenyl, furyl, thienyl and mono-substituted phenyl, wherein the substituent is fluoro, chloro, bromo, alkyl having 1 to 3 carbons, alkoxy having 1 to 3 carbons or trifluoromethyl.

Said compounds of formula I are useful for administration to a mammalian subject to inhibit, i.e., prevent or cure, gastric ulcers. Accordingly, this invention also provides a method of inhibiting gastric ulcers in a mammalian subject, and pharmaceutical compositions suitable for administration to a mammalian subject to inhibit gastric ulcers.

A preferred group of compounds of this invention consists of the compounds of formula I, wherein $R^3$ is methyl and $R^1$ and $R^2$ are as defined previously. Within this preferred group, particularly preferred compounds are those in which $R^2$ and $R^3$ are each methyl and $R^1$ is as defined previously. Especially preferred individual compounds of the invention are:

2-guanidino-4-(5-[N,N-dimethylaminomethyl]-2-furyl)-thiazole (I, wherein $R^1$ is H and $R^2$ and $R^3$ are $CH_3$), 2-(3-n-hexylguanidino)-4-(5-[N,N-dimethylaminomethyl]2-furyl)thiazole (I, wherein $R^1$ is n-hexyl and $R^2$ and $R^3$ are each methyl)

and the pharmaceutically-acceptable acid-addition salts thereof.

DETAILED DESCRIPTION

The antiulcer compounds of this invention can be prepared, for example, by the method shown in Scheme A, wherein $R^1$, $R^2$ and $R^3$ are as defined previously and X is bromo or chloro.

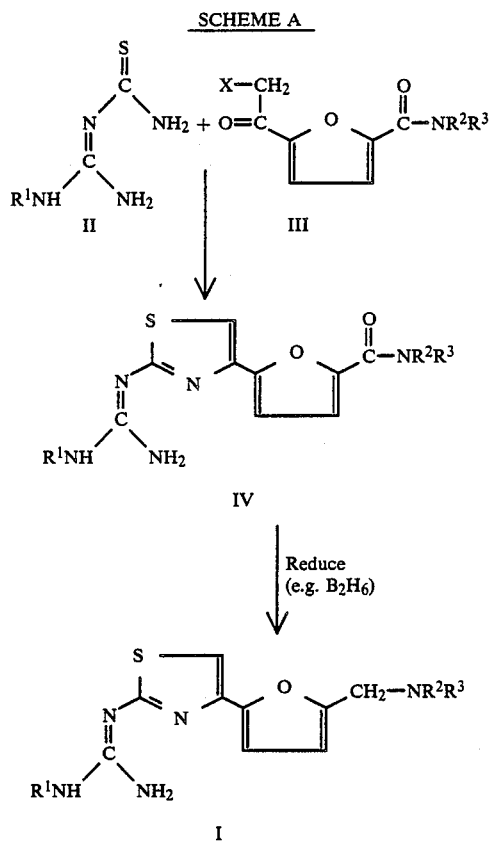

In the first step of Scheme A, the appropriate guanylthiourea of the formula II is condensed with a haloketone, and preferably a bromo-ketone, of the formula III. This reaction is usually carried out by contacting the halo-ketone with an equimolar amount or a slight excess of the guanylthiourea in a suitable, reaction-inert solvent. A suitable, reaction-inert solvent is one which will substantially dissolve at least one of the reactants, and which does not adversely interact with either of the reactants or the product. It is often convenient to use a volatile solvent. Typical solvents which can be used are lower-alkanols, e.g. methanol or ethanol; low-molecular weight ketones, such as acetone or methylisobutyl ketone; low-molecular weight esters, such as ethyl acetate; low-molecular weight ethers, such as 1,2-dimethoxyethane or tetrahydrofuran; acetonitrile; dipolar, aprotic solvents, such as N,N-dimethylformamide, N-methylpyrrolidone or dimethyl sulfoxide; or mixtures of these solvents. Acetone and N,N-dimethylformamide are preferred. The reaction is usually carried out at a temperature from 20° to 100° C., preferably from 25° to 60° C. Using a temperature in this latter range, reaction times of a few hours, e.g. two to 10 hours are normally sufficient, but at the lower end of the temperature range the reaction is sometimes allowed to proceed for several days to ensure essentially complete conversion to thiazole IV.

The thiazole compound of formula IV can be isolated by standard methods. If the product is out of solution at the end of the reaction, it can be recovered by filtration (as the hydrohalide salt). Alternatively, if the product is not out of solution at the end of the reaction, it can be recovered (as the hydrohalide salt) by solvent evaporation, or by precipitation by the addition of a non-solvent followed by filtration. The hydrohalide salt is readily converted to the free base by standard neutralization/extraction methods. The thiazole of formula IV or salt thereof can be purified by standard methods, e.g. recrystallization, if desired. Alternatively, it can be used in the crude state for conversion into a compound of formula I.

The second step of Scheme A involves treatment of the thiazole IV with a reagent which will reduce the amide grouping of the formula $-CO-NR^2R^3$ to an amine grouping of the formula $-CH_2-NR^2R^3$. Several reagents known for this type of transformation can be used; however, the reducing agent chosen must not affect the rest of the molecule in either the starting thiazole IV or the product of formula I. A convenient reagent which can be used is diborane.

When a thiazole of formula IV is reduced to a compound of formula I using diborane, the compound of formula IV is contacted with from 0.8 to 4.0 molar equivalents, and preferably substantially one molar equivalent, of diborane in a suitable, reaction-inert solvent at a temperature in the range from 0° to 50° C., and preferably 20° to 30° C. A suitable, reaction-inert solvent is one which will substantially dissolve at least one of the reactants, and will not interact adversely with either the thiazole IV, diborane or the product of formula I. Typical solvents which can be used for this reduction are ethers, such as diethyl ether, 1,2-dimethoxyethane, tetrahydrofuran and dioxan, or mixtures thereof. The reduction proceeds quite quickly, and normally it is complete within a few hours at about room temperature. The reaction mixture is then treated with an excess of aqueous acid, cautiously at first, and then the resulting mixture is made alkaline. The product can then be isolated by extraction into a water-immiscible, volatile, organic solvent, followed by evaporation of the solvent. The compound of formula I thus obtained can be purified by standard methods, such as recrystallization or chromatography, if desired.

The guanylthiourea compounds of the formula II can be prepared by reaction of the appropriate N-cyanoguanidine of the formula V with gaseous hydrogen sulfide, viz:

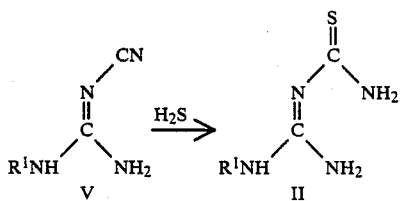

This reaction is usually carried out in an organic solvent such as a $(C_1-C_4)$alkanol or ethyl acetate, preferably methanol, in the presence of a catalytic amount of a secondary amine, preferably diethylamine. The reaction can be carried out at atmospheric pressure or a higher pressure, e.g. at 3 to 10 kg/cm², and at a temperature of from about 10° to 100° C., preferably from 25° to 80° C. Of course, when the reaction is run at a higher temperature within the preferred range, the reaction time will be shorter. Conversely, at a lower temperature the reaction time required will be longer. The product is ordinarily isolated simply by evaporation of the solvent. In many cases the crude product is of sufficient purity for use in the next reaction step. Alternatively, the crude product can be purified, e.g. by column chromatography.

The N-cyanoguanidine compounds V are prepared by reaction of the appropriate amine and dicyanimide in approximately equimolar amounts by methods described by Curd et al., *J. Chem. Soc.*, 1630 (1948) and by Redmon and Nagy in U.S. Pat. No. 2,455,807, as follows:

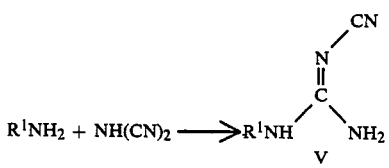

Typically, the reactants are heated in the presence of a polar organic solvent, e.g. a $(C_1-C_4)$alkanol, water or mixtures thereof, at a temperature of from 40° to 120° C., preferably at the reflux temperature of the solvent. The N-cyanoguanidine product can be isolated by cooling, filtering to remove precipitated salts, and evaporating the filtrate.

The halo-ketones of the formula III can be prepared by halogenation of the appropriate acetylfuran of the formula VI, viz:

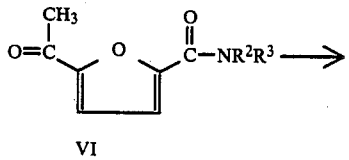

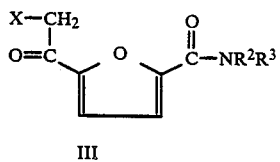

wherein X is bromo or chloro. This can be carried out by standard methods for the bromination or chlorination of methyl ketones. For example, when X is bromo, the ketone VI is treated with one molar equivalent, or a slight excess, of elemental bromine in glacial acetic acid solution, at about room temperature, for about 20 hours. The bromo-ketone is isolated simply by removal of the solvent by evaporation, and it can be purified, if desired by standard solvent extraction and/or recrystallization techniques.

The corresponding 4-chloroacetylfuran intermediates of formula III, where X is chloro, can be prepared from the appropriate compound of formula VI, typically by reaction with sulfuryl chloride. The compound VI is dissolved in methylene chloride and dry hydrogen chloride is added. An equimolar amount of sulfuryl chloride is then added at room temperature and the chloro-ketone isolated by standard methods.

The compounds of formula VI are prepared from the known compound, 5-acetylfuran-2-carboxylic acid (*Journal of Organic Chemistry*, 32, 2917 [1967]). This involves conversion of an acid to a tertiary amide, and it is carried out by standard methods, well-known in the art. For example, the 5-acetylfuran-2-carboxylic acid is activated, either by acid chloride formation using thionyl chloride or by mixed anhydride formation by reaction of a carboxylate salt with ethyl chloroformate, and the activated derivative thus obtained is reacted with the requisite amine of formula $R^2R^3NH$.

The antiulcer compounds of the formula I are basic and therefore they will form acid-addition salts. All such salts are within the scope of this invention, although for administration to a mammalian subject it is necessary to use a pharmaceutically-acceptable salt. The compounds of formula I contain more than one basic center, and both mono-and di-acid-addition salts can be prepared. For di-acid-addition salts, the anionic counter ions can be the same or different. In general, for preparation of the acid-addition salts, the compound of formula I is combined with a stoichiometric amount of an appropriate acid in an inert solvent, which can be aqueous, partially aqueous or non-aqueous. The salt is then recovered by solvent evaporation, by filtration if the salt precipitates spontaneously, or by precipitation using a non-solvent followed by filtration. Typical salts which can be prepared include sulfate, hydrochloride, hydrobromide, nitrate, phosphate, citrate, tartrate, pamoate, sulfosalicylate, methanesulfonate, benzenesulfonate and 4-toluenesulfonate salts.

As indicated hereinbefore, the compounds of this invention are useful as antiulcer compounds in mammals. This activity can be demonstrated in experimental animals either by measuring their ability to inhibit gastric acid secretion and/or by measuring their cytoprotective activity. The ability of the compounds of the invention to inhibit gastric acid secretion can be measured either directly (see Example 6) or by measuring their histamine $H_2$-antagonist properties (see Example 7). The cytoprotective activity of the compounds of the invention can be measured by their ability to inhibit ethanol-induced gastric ulceration in rats (see Example 8).

For the purpose of inhibiting gastric ulcers in a mammalian subject, i.e. for the prophylactic or curative treatment of gastric ulcers, a compound of this invention of the formula I, or a pharmaceutically-acceptable acid-addition salt thereof, can be administered to a mammal subject either orally or parenterally. Although the precise dosage will be chosen by the prescribing physician, by the oral route an effective gastric ulcer inhibiting dosage will normally be in the range from 0.5 to 100 mg/kg of body weight per day, and preferably 1 to 20 mg/kg of body weight per day, in single or divided doses. In like manner, by the parenteral route an effective gastric ulcer inhibiting dosage will normally be in the range from 0.5 to 25 mg/kg of body weight per day, and preferably 0.5 to 5 mg/kg of body weight per day, in single or divided doses.

An antiulcer compound of this invention can be administered to a mammalian subject alone, or, preferably, in combination with a pharmaceutically-acceptable carrier in a pharmaceutical composition, in accordance with standard pharmaceutical practice. Suitable pharmaceutical carriers include inert diluents or fillers, water and various organic solvents. The pharmaceutical compositions formed by combining the novel compounds of formula I or salt thereof with pharmaceutically-acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, can be employed, together with various disintegrants such as starch, alginic acid and certain complex silicates, and with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, proplyene glycol, glycerin, or combinations thereof.

Preferably, the products of this invention are administered orally in unit dosage form, i.e. as a single, physically-discrete dosage unit containing an appropriate amount of the active compound in combination with a pharmaceutically acceptable carrier. Examples of such unit dosage forms are tablets or capsules containing from about 5 to 1,000 mg of the active ingredient, and in which the weight ratio of said active ingredient to said carrier is in the range from 1:1 to 1:20.

For parenteral administration, solutions or suspensions of the compound of formula I in sterile aqueous solutions, for example aqueous propylene glycol, sodium chloride, dextrose or sodium bicarbonate solutions are employed. Such dosage forms can be suitably buffered, if desired.

The following examples and preparations are being provided solely for the purose of further illustration. Proton nuclear magnetic resonance (NMR) spectra were measured at 60 MHz, and peak positions are reported in parts per million (ppm) downfield from internal tetramethylsilane. The following abbreviations for peak shapes are used: s, singlet; bs, broad singlet; t, triplet; bt, broad triplet; q, quartet; m, multiplet.

EXAMPLE 1

2-Guanidino-4-(5-[N,N-dimethylaminomethyl]-2-furyl)thiazole

To a stirred solution of 676 mg. (2.43 mmole) of 2-guanidino-4-(5-[N,N-dimethylcarbamoyl]-2-furyl)-thiazole in 25 ml. of tetrahydrofuran was added dropwise, at room temperature, 24.9 ml. (24.3 mmole) of a 0.97M solution of diborane in tetrahydrofuran. Stirring was continued for 5 hours at room temperature and then 15 ml. of 6N hydrochloric acid was added slowly, keeping the temperature below 30° C. Stirring was continued for 30 minutes, and then the mixture was diluted with water and washed with ethyl acetate. The resulting aqueous phase was made alkaline with 1N sodium hydroxide solution and the solid which precipitated was recovered by filtration, to give 340 mg. of the title compound, mp greater than 200° C.

EXAMPLE 2

2-Guanidino-4-(5-[N,N-dimethylaminomethyl]-2-furyl)thiazole Dihydrobromide

The product of Example 1 was dissolved in a small volume of a mixture of ethanol and diethyl ether, and to the solution was added an excess of ethereal hydrogen bromide. The resulting mixture was boiled until the ether had been removed by distillation and all the solid was in solution. The resulting solution was cooled, and the solid which precipitated was recovered by filtration to give a first crop of the title salt, 246 mg, mp 251°–253° C. A second crop, 84 mg, mp 249°–250° C., was obtained from the filtrate. EXAMPLE 2 (Cont.)

The NMR spectrum (CD$_3$OD/D$_2$O) of a sample of the title product from an analogous preparation showed absorptions at 2.9 (s, 6H), 4.5 (s, 2H), 6.9 (s, 2H) and 7.8 (s, 1H) ppm.

Analysis: Calcd. for C$_{11}$H$_{15}$N$_5$OS.2HBr: C, 30.93; H, 4.01; N, 16.39%. Found: C, 31.31; H, 4.07; N, 16.41%.

EXAMPLE 3

2-Guanidino-4-(5-[N-n-hexyl-N-methylaminomethyl]-2-furyl)thiazole

2-Guanidino-4-(5-[N-n-hexyl-N-methylcarbamoyl]-2-furyl)thiazole (2.0 g., 4 mmole) was reduced with an excess of diborane in tetrahydrofuran substantially according to the procedure of Example 1. At the end of the reduction, 15 ml. of 6N hydrochloric acid was added and the resulting mixture was heated under reflux for 25 minutes. The cooled mixture was then made alkaline with 10N sodium hydroxide solution and the solid which precipitated was removed by filtration. The remaining aqueous phase was extracted with n-butanol, and the extracts were dried (Na$_2$SO$_4$) and evaporated. The residue was purified by column chromatography on silica gel using 1:5 methanolchloroform as eluant, giving two crops of the title compound, 300 mg. and 460 mg.

The above two crops were converted into the dihydrobromide salt and recrystallized from diethyl ether-ethanol. Total yield: 390 mg., mp 207°–209° C.

Analysis: Calcd. for C$_{16}$H$_{25}$N$_5$OS.2HBr: C, 38.64; H, 5.47; N, 14.08%. Found: C, 38.53; H, 5.24; N, 14.05%.

EXAMPLE 4

2-(3-n-Hexylguanidino)-4-(5-[N,N-dimethylaminomethyl]-2-furyl)thiazole 2-(3-n-Hexylguanidino)-4-(5-[N,N-dimethylcarbamoyl]-2-furyl)thiazole (1.77 g., 4 mmole) was reduced with an excess of diborane in tetrahydrofuran, substantially according to the procedure of Example 1. At the end of the reduction, 20 ml. of 6N hydrochloric acid was added dropwise, very slowly, and then the mixture was heated at ca 90° C. to removed the majority of the tetrahydrofuran. The aqueous residue was made alkaline with 10N sodium hydroxide solution and then it was extracted with n-butanol. The dried (Na$_2$SO$_4$) extracts were evaporated in vacuo to give a dark-colored oil which was purified by chromatography on silica gel using 1:10 methanol-chloroform. This afforded the title compound, 950 mg, as an oil.

The above oil was dissolved in a small volume of acetone, and 0.6 ml. of aqueous hydrogen bromide (2 equivalents) was added. The resulting mixture was heated at ca 90° C. for 30 minutes, and then it was cooled. The solid which precipitated was recovered by filtration to give the dihydrobromide of the title compound, 450 mg., mp 207°–209° C.

Analysis: Calcd. for $C_{17}H_{27}N_5OS \cdot 2HBr$: C, 39.93; H, 5.71; N, 13.69%. Found: C, 39.86; H, 5.68; N, 13.96%.

EXAMPLE 5

The compounds in Table I below can be prepared by reduction of the appropriate 2-guanidino-4-(5-(N,N-disubstituted-carbamoyl]-2-furyl)thiazole with diborane in tetrahydrofuran, using the procedure of Example 1.

TABLE I

| $R^1$ | $R^2$ | $R^3$ |
|---|---|---|
| methyl | methyl | 3-trifluoromethylbenzyl |
| benzyl | ethyl | 2-isopropoxybenzyl |
| 2-phenylethyl | isopropyl | 4-methoxybenzyl |
| 3-phenylpropyl | methyl | 3-isopropylbenzyl |
| 2-furylmethyl | methyl | methyl |
| 3-thienylmethyl | methyl | n-hexyl |
| 2-(3-fluorophenyl)ethyl | methyl | 3-(2-tolyl)propyl |
| 3-chlorobenzyl | ethyl | t-butyl |
| 4-bromobenzyl | methyl | 2-thienylmethyl |
| 3-(2-tolyl)propyl | n-hexyl | isopropyl |
| 3-isopropylbenzyl | methyl | methyl |
| 4-methoxybenzyl | ethyl | 3-furylmethyl |
| 2-(2-isopropoxyphenyl)ethyl | methyl | 2-phenylethyl |
| 3-trifluoromethylbenzyl | isopropyl | 2-fluorobenzyl |
| ethyl | methyl | 4-chlorobenzyl |
| t-butyl | methyl | 3-bromobenzyl |

EXAMPLE 6

Gastric Acid Antisecretory Activity

The gastric acid antisecretory activity of compounds of the present invention was determined in overnight-fasted, conscious Heidenhain pouch dogs as follows:

Pentagastrin (Pentavlon-Ayerst) is used to stimulate acid output by continuous infusion into a superficial leg vein at doses earlier determined to stimulate near maximal acid output from the gastric pouch. Gastric juice is collected at 30 minute intervals following the start of a pentagastrin infusion and measured to the nearest 0.1 ml. Ten collections are taken for each dog during an experiment. Acid concentration is determined by titrating 1.0 ml. of gastric juice to pH 7.4 with 0.1N sodium hydroxide using an Autoburette and a glass electrode pH meter (Radiometer).

Drug or vehicle is given intravenously or orally 90 minutes following the start of the pentagastrin infusion, at a dose of 2 mg/kg or less. Gastric acid antisecretory effects are calculated by comparing the lowest acid output after drug administration with the mean acid output immediately before drug.

At a dosage of 0.1 mg/kg. (intravenously), the products of Examples 2, 3 (2HBr salt) and 4 (2HBr salt) gave 44, 24 and 38% inhibition, respectively.

EXAMPLE 7

Histamine-$H_2$ Antagonist Activity

The histamine-$H_2$ antagonist activity of compounds of the present invention was determined by the following procedure:

Guinea pigs are killed rapidly with a blow to the head, the heart removed and the right atria dissected free. Atria are suspended, isometrically, in a temperature-controlled (32°±2° C.) tissue bath (10 ml.) containing oxygenated (95% $O_2$; 5% $CO_2$) Krebs-Henseleit buffer (pH 7.4) and are allowed to stabilize approximately one hour during which time the tissue bath is flushed several times. Individual atrial contractions are followed with a force-displacement transducer connected to a cardiotachometer and Grass polygraph recorder. After obtaining a dose-response curve to histamine, the bath containing each atrium is flushed several times with fresh buffer and the atria re-equilibrated to basal rates. Following the return to basal rate, test compounds are added at selected final concentrations and the histamine dose-response curve is again determined in the presence of antagonist. Results are expressed as dose-ratios, the ratio of histamine concentrations required to produce one-half of maximal stimulation in the presence and absence of antagonist, and the apparent dissociation constant of the $H_2$-receptor antagonist $pA_2$, is determined.

The products of Examples 2, 3 (2HBr salt) and 4 (2HBr salt) gave $pA_2$ values of 7.7, 7.0 and 6.0, respectively.

EXAMPLE 8

Inhibition of Ethanol-Induced Ulceration in Rats

The antiulcer activity of the products of this invention was determined by an ethanol-induced rat ulcer assay. In this test, overnight fasted male rats are given drug (at 30 or 3 mg/kg) or water orally fifteen minutes prior to an orally administered dose of absolute ethanol (1.0 ml.). One hour after the ethanol challenge the animals (8/group) are killed and the stomachs examined for the presence of lesions. After sacrifice the abdomen is opened and a locking hemostat placed at the pylorus. Six ml. of a 4% solution of formaldehyde is injected into the stomach with a gastric feeding tube and a second locking hemostat is used to seal the esophagus. The stomach is removed, opened along the greater curvature and examined for ulceration.

The scoring system used to quantitate the ethanol-induced lesions is given below.

| Ulcer Score Table | |
|---|---|
| Score | Definition |
| 1 | Normal appearing stomach |
| 2 | Pinpoint sized lesions |
| 3 | Lesions, 2 or fewer; pinpoint lesions may be present |
| 4 | Lesions, >2; pinpoint lesions may be present |
| 5 | Lesions with hemorrage |

For each group of animals an ulcer index is calculated as follows: EXAMPLE 8 (Cont.)

Ulceration Index=(the sume of the scores of the group)×(the sum of the number of ulcers in the group)×(the fraction of the group havnng any incidence of ulceration).

The percentage inhibition of ulcers is calculated as follows:

% Inhibition=100×[(ulcer index controls) - (ulcer index drug-treated)]≧(ulcer index controls).

At an oral dose of 30 mg/kg., the products of Examples 2, 3 (2HBr salt) and 4 (2HBr salt) showed 7, 49 and 93% inhibition of ethanol-induced ulceration, respectively.

PREPARATION 1

5-Acetylfuran-2-carboxylic Acid

A solution of 25.2 g. (0.2 mole) of methyl furan2-carboxylate in 75.6 ml. (0.8 mole) of acetic anhydride was prepared at −10° C., and then to this solution was added, dropwise, with stirring, at −10° C., 46.4 ml. (0.4 mole) of stannic chloride ($SnCl_4$). The resulting mixture was allowed to warm to room temperature, and then stirring was continued at room temperature overnight. The reaction mixture was then cooled in an ice-bath, and 25 ml. of concentrated hydrochloric acid was added, with stirring. After 1 hour, the mixture was diluted with water and extracted with ethyl acetate. The extracts were washed with water, dried ($Na_2SO_4$) and evaporated in vacuo. The residue, an oil, was purified by chromatography on silica gel, eluting with chloroform, to give 32 g. of methyl 5-acetoacetylfuran-2-carboxylate as an orange solid, mp 89°–95° C.

The above methyl 5-acetoacetylfuran-2-carboxylate, 300 ml. of ethanol and 300 ml. of 1N sodium hydroxide solution were combined and heated under reflux for 1.5 hours. The reaction mixture was cooled, reduced to a smaller volume by evaporation in vacuo, acidified using 6N hydrochloric acid, and extracted with chloroform. The extracts were dried and evaporated in vacuo to give 6.2 g. of 5-acetylfuran-2-carboxylic acid as a yellow solid. The aqueous phases from the chloroform extractions was then further extracted with chloroform in a continuous extractor for 18 hours. The latter chloroform extract was dried and evaporated in vacuo to give an additional 14.5 g of 5-acetylfuran-2carboxylic acid as a solid, mp 189°–195° C.

PREPARATION 2

5-Acetylfuran-2-carbonyl Chloride

A mixture of 8.2 g. (0.053 mole) of 5-acetyl-2-furoic acid and 200 ml. of thionyl chloride was heated under reflux for 2.5 hours and then it was cooled to room temperature. The mixture was concentrated in vacuo, and the residue was dissolved in toluene. The resulting solution was evaporated in vacuo to give 9.1 g. of 5-acetylfuran-2-carbonyl chloride as a solid.

PREPARATION 3

N,N-Dimethyl-5-acetylfuran-2-carboxamide

To a stirred solution of 9.1 g. (0.053 mole) of 5-acetylfuran-2-carbonyl chloride in 150 ml. of tetrahydrofuran at ca −30° C. was added, dropwise, 7.0 ml. (0.106 mole) of dimethylamine. Stirring was continued, and the reaction mixture was allowed to warm to room temperature and then stirred overnight. The tetrahydrofuran was removed by evaporation in vacuo, and the residue was diluted with water and extracted with ethyl acetate. The extracts were washed with water, dried ($MgSO_4$) and concentrated in vacuo. The residue was purified by chromatography on silica gel, eluting with 1:20 methanol-chloroform, to give 7.33 g. of the title compound as a solid, mp 101°–104° C. A small sample was recrystallized from cyclohexane to give a pale yellow solid, mp. 104°–106° C.

PREPARATION 4

N-n-Hexyl-N-methyl-5-acetylfuran-2-carboxamide

To a stirred slurry of 4.6 g. (0.03 mole) of 5-acetylfuran-2-carboxylic acid in 150 ml. of dichloromethane was added 3.3 g. (0.033 mole) of N-methylmorpholine. The resulting solution was cooled to −20° C., and 3.6 g. (0.033 mole) of ethyl chloroformate was added dropwise, with stirring. Stirring was continued for 1 hour at −15° C. and then 3.8 g. (0.033 mole) of n-hexylmethylamine was added dropwise at −20° C. The resulting mixture was stirred for 1.5 hours while being allowed to warm to room temperature. The reaction mixture was then washed with water, dried ($Na_2SO_4$) and evaporated in vacuo to give 7.5 g. of an oil. This oil was chromatographed on silica gel, eluting with 1:1 hexane-ethyl acetate, to give 5.6 g. of the title amide as an oil.

The NMR spectrum of the product ($CDCl_3$) showed absorptions at 0.6–1.8 (m, 11H), 2.4 (s, 3H), 3.1 (bs, 3H), 3.6 (bt, 2H) and 7.1 (q, 2H) ppm.

PREPARATION 5

The following compounds can be prepared by conversion of 5-acetylfuran-2-carboxylic acid into a mixed anhydride with ethyl chloroformate, followed by reaction with the appropriate amine of the formula $R^2R^3NH$, using the procedure of Preparation 4:

N-methyl-N-(3-trifluoromethylbenzyl)-5-acetylfuran-2-carboxamide,

N-ethyl-N-(2-isopropoxybenzyl)-5-acetylfuran-2-carboxamide,

N-isopropyl-N(4-methoxybenzyl)-5-acetylfuran-2-carboxamide,

N-methyl-N-(3-isopropylbenzyl)-5-acetylfuran-2-carboxamide,

N-methyl-N-(3-[2-tolyl]propyl)-5-acetylfuran-2-carboxamide,

N-ethyl-N-t-butyl-5-acetylfuran-2-carboxamide,

N-methyl-N-(2-thienylmethyl)-5-acetylfuran-2-carboxamide,

N-n-hexyl-N-isopropyl-5-acetylfuran-2-carboxamide,

N-ethyl-N-(3-furylmethyl)-5-acetylfuran-2-carboxamide,

N-methyl-N-(2-phenylethyl)-5-acetylfuran-2-carboxamide,

N-isopropyl-N-(2-fluorobenzyl)-5-acetylfuran-2-carboxamide,

N-methyl-N-(4-chlorobenzyl)-5-acetylfuran-2-carboxamide and

N-methyl-N-(3-bromobenzyl)-5-acetylfuran-2-carboxamide.

PREPARATION 6

N,N-Dimethyl-5-(2-bromoacetyl)furan-2-carboxamide

A mixture of 1.81 g. (0.01 mole) of N,N-dimethyl-5-acetylfuran-2-carboxamide, 1.59 g. (0.01 mole) of bromine and 40 ml. of glacial acetic acid was stirred at room temperature for 18 hours, and then the acetic acid was removed by evaporation in vacuo. The residue was partitioned between water and ethyl acetate and the layers were separated. The aqueous layer was further extracted with ethyl acetate, and the combined ethyl acetate solutions were washed with sodium bicarbonate solution followed by water, dried ($Na_2SO_4$) and evaporated in vacuo. This afforded 2.6 g. of the title compound as a solid.

PREPARATION 7

N-n-Hexyl-N-methyl-5-(2-bromoacetyl)furan-2-carboxamide

The title compound was prepared by bromination of 5.0 g. of N-n-hexyl-N-methyl-5-acetylfuran-2-carboxamide using the procedure of Preparation 6, except that that reaction was conducted at room temperature for 1.5 hours followed by 50 minutes at 50° C. Yield: 6.8 g. of an oil.

The NMR spectrum (CDCl3) showed absorptions at 0.7-2.0 (m, 11H), 3.3 (bs, 3H), 3.6 (bt, 2H), 4.3 (s, 2H) and 7.1 (q, 2H) ppm.

PREPARATION 8

The following bromoacetyl compounds can be prepared by bromination of the appropriate compound from Preparation 5, using the procedure of Preparation 6:

N-methyl-N-(3-trifluoromethylbenzyl)-5-(2-bromoacetyl)furan-2-carboxamide,
N-ethyl-N-(2-isopropoxybenzyl)-5-(2-bromoacetyl)furan-2-carboxamide,
N-isopropyl-N-(4-methoxybenzyl)-5-(2-bromoacetyl)-furan-2-carboxamide,
N-methyl-N-(3-isopropylbenzyl)-5-(2-bromoacetyl)furan-2-carboxamide,
N-methyl-N-(3-[2-tolyl]propyl)-5-(2-bromoacetyl)furan-2-carboxamide,
N-ethyl-N-t-butyl-5-(2-bromoacetyl)furan-2-carboxamide,
N-methyl-N-(2-thienylmethyl)-5-(2-bromoacetyl)furan-2carboxamide,
N-n-hexyl-N-isopropyl-5-(2-bromoacetyl)furan-2-carboxamide,
N-ethyl-N-(3-furylmethyl)-5-(2-bromoacetyl)furan-2-carboxamide,
N-methyl-N-(2-phenylethyl)-5-(2-bromoacetyl)furan-2-carboxamide,
N-isopropyl-N-(2-fluorobenzyl)-5-(2-bromoacetyl)furan-2-carboxamide, PREPARATION 8 (Cont.)
N-methyl-N-(4-chlorobenzyl)-5-(2-bromoacetyl)furan-2-carboxamide and
N-methyl-N-(3-bromobenzyl)-5-(2-bromoacetyl)furan-2-carboxamide.

PREPARATION 9

2-Guanidino-4-(5-[N,N-dimethylcarbamoyl]-2-furyl)-thiazole

A mixture of 2.6 g. (0.01 mole) of N,N-dimethyl5-(2-bromoacetyl)furan-2-carboxamide, 1.18 g. (0.01 mole) of guanylthiourea and 100 ml. of acetone was stirred at room temperature for 4 hours. An additional 354 mg. of guanylthiourea was added and stirring was continued for 3 days. The reaction mixture was filtered, and the residue was washed with acetone and then dissolved in water. The solution thus obtained was made alkaline using 10% sodium hydroxide solution and extracted with ethyl acetate. The extracts were dried (MgSO4) and concentrated in vacuo to give a first crop of the title compound (500 mg.). The aqueous phase from the extraction was further basified (to pH 14) and extracted with n-butanol. Evaporation of the n-butanol gave a second crop of the title compound (900 mg.). The two crops of the title compound were combined and recrystallized from aqueous ethanol, giving 550 mg. of a brown solid, mp. 252°-253.5° C. (dec). Two additional samples of the title compound were obtained from the recrystallization mother liquors: 190 mg. mp 249°-252° C.; 91 mg., mp 248°-251° C.

Further recrystallization from aqueous ethanol of the title material having a melting point of 252°-253.5° C. (dec.) raised the melting point to 253°-254° C.

PREPARATION 10

2-Guanidino-4-(5-[N-n-hexyl-N-methylcarbamoyl]-2-furyl)thiazole Hydrobromide

A mixture of 6.8 g. (0.02 mole) of N-n-hexyl-N- methyl-5-(2-bromoacetyl)furan-2-carboxamide, 2.4 g. (0.02 mole) of guanylthiourea and 225 ml. of acetone was stirred at room temperature for 2 hours. The solid was recovered by filtration (5.4 g.) and recrystallized from ethanol to give 812 mg. of the title compound as a white solid, mp. 226°-228° C.

The mother liquors from the recrystallization were evaporated in vacuo to give an oil to which was added acetone, and then the resulting mixture was heated. The solid which formed was recovered by filtration to give an additional 4.0 g. of the title compound.

PREPARATION 11

2-(3-n-Hexylguanidino)-4-(5-[N,N-dimethylcarbamoyl]-2-furyl)thiazole Hydrobromide A mixture of 2.6 g. (0.01 mole) of N,N-dimethyl5-(2-bromoacetyl)furan-2-carboxamide, 2.02 g. (0.01 mole) of (N-n-hexylguanyl)thiourea and 75 ml. of acetone was heated under reflux for 4 hours, and then it was cooled and filtered. This gave 2.3 g. of the title compound as a white solid, mp. 155°-158° C.

PREPARATION 12

The compounds in Table II can be prepared by reaction of the appropriate N,N-disubstituted-5-(2-bromoacetyl)furan-2-carboxamide from Preparation 6, 7 or 8 with the requisite guanylthiourea, using the procedure of Preparation 11.

TABLE II

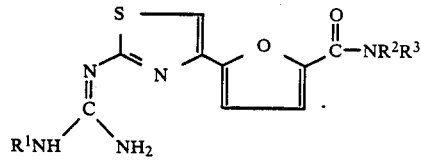

| R1 | R2 | R3 |
|---|---|---|
| methyl | methyl | 3-trifluoromethylbenzyl |
| benzyl | ethyl | 2-isopropoxybenzyl |
| 2-phenylethyl | isopropyl | 4-methoxybenzyl |
| 3-phenylpropyl | methyl | 3-isopropylbenzyl |
| 2-furylmethyl | methyl | methyl |
| 3-thienylmethyl | methyl | n-hexyl |
| 2-(3-fluorophenyl)ethyl | methyl | 3-(2-tolyl)propyl |
| 3-chlorobenzyl | ethyl | t-butyl |
| 4-bromobenzyl | methyl | 2-thienylmethyl |
| 3-(2-tolyl)propyl | n-hexyl | isopropyl |
| 3-isopropylbenzyl | methyl | methyl |
| 4-methoxybenzyl | ethyl | 3-furylmethyl |
| 2-(2-isopropoxyphenyl)ethyl | methyl | 2-phenylethyl |
| 3-trifluoromethylbenzyl | isopropyl | 2-fluorobenzyl |
| ethyl | methyl | 4-chlorobenzyl |
| t-butyl | methyl | 3-bromobenzyl |

PREPARATION 13

(3-n-Hexylguanyl)thiourea

Gaseous hydrogen sulfide was bubbled through a mixture of 4.5 g. (0.027 mole) of 1-cyano-3-n-hexylguanidine, 75 ml. of methanol and 0.5 ml. of diethylamine for 6 hours, with stirring. Stirring was continued for 16 hours and then the mixture was heated to reflux temperature and hydrogen sulfide was again bubbled through the mixture. The resulting mixture was heated under reflux for an additional 16 hours, and then it was cooled to room temperature and evaporated in vacuo. The residue was chromatographed on silica gel, eluting with 1:9 methanol-chloroform to give 4.4 g. of the title compound as a solid.

PREPARATION 14

1-Cyano-3-n-hexylguanidine

A mixture of 13.8 g. (0.10 mole) n-hexylamine hydrochloride 8.9 g. (0.125 mole), dicyanimide and 75 ml. n-butanol were stirred while heating at reflux for three hours. The mixture was then cooled, filtered to remove precipitated salt, and the filtrate evporated to a syrup and crystallized from dioxan. Mass spectrum (m/e): 169 molecular ion.

I claim:

1. A 2-guanidino-4-(2-furyl)thiazole compound of the formula

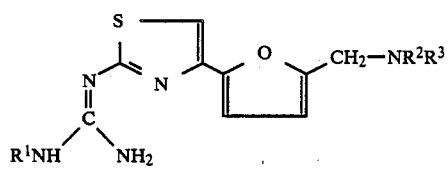

and the pharmaceutically-acceptable acid-addition salts thereof, wherein $R^1$ is selected from the group consisting of hydrogen, alkyl having 1 to 6 carbons and —$(CH_2)_m$—W;
$R^2$ is alkyl having 1 to 6 carbons; and $R^3$ is alkyl having 1 to 6 carbons or —$(CH_2)_n$—Z;
wherein m and n are each 1, 2 or 3; and W and Z are each selected from the group consisting of phenyl, furyl, thienyl and monp-substituted phenyl, wherein the substituent is fluoro, chloro, bromo, alkyl having 1 to 3 carbons, alkoxy having 1 to 3 carbons or trifluoromethyl.

2. A compound according to claim 1, wherein $R^3$ is said alkyl.

3. A compound according to claim 2, wherein $R^3$ is methyl.

4. A compound according to claim 3, wherein $R^2$ is n-hexyl.

5. A compound according to claim 4, wherein $R^1$ is hydrogen.

6. A compound according to claim 3, wherein $R^2$ is methyl.

7. A compound according to claim 6, wherein $R^1$ is hydrogen.

8. A compound according to claim 6, wherein $R^1$ is said alkyl.

9. A compound according to claim 8, wherein $R^1$ is n-hexyl.

10. A method of inhibiting gastric ulcers in a mammalian subject in need of such treatment, which comprises administering to said subject an effective gastric ulcer inhibiting amount of a 2-guanidino-4-(2-furyl)thiazole compound according to claim 1.

11. The method according to claim 10, wherein $R^2$ and $R^3$ are each methyl.

12. The method according to claim 11, wherein $R^1$ is hydrogen.

13. A pharmaceutical composition, useful for inhibiting gastric ulcers in a mammalian subject, which comprises a pharmaceutically-acceptable carrier and a 2-guanidino-4-(2-furyl)thiazole compound according to claim 1, wherein the weight ratio of said 2-guanidino-4-(2-furyl)thiazole compound to said carrier is in the range from 1:1 to 1:20.

* * * * *